United States Patent [19]

Buchan et al.

[11] Patent Number: 5,026,860

[45] Date of Patent: Jun. 25, 1991

[54] BIDENTATE CHELATING MONOMERS AND POLYMERS

[75] Inventors: Gavin M. Buchan, Harlow; Ian J. Ferguson, Ickleton, both of England

[73] Assignee: Minnesota Mining and Manufacturing Company, St. Paul, Minn.

[21] Appl. No.: 675,127

[22] Filed: Nov. 27, 1984

Related U.S. Application Data

[63] Continuation-in-part of Ser. No. 527,333, Aug. 29, 1983, abandoned.

[51] Int. Cl.$^5$ ............................................. C07D 235/04
[52] U.S. Cl. .................................... 546/271; 546/14; 548/325; 548/330; 548/333; 548/4
[58] Field of Search ................... 526/259; 546/14, 271; 548/325, 330, 333, 334

[56] References Cited

U.S. PATENT DOCUMENTS

| | | | |
|---|---|---|---|
| 2,634,253 | 4/1953 | Maynard | 260/47 |
| 3,165,487 | 1/1965 | Gardner et al. | 260/29.7 |
| 3,304,276 | 2/1967 | Faulkner et al. | 260/22 |
| 3,395,134 | 7/1968 | d'Alelio | 260/89.5 |
| 4,011,204 | 3/1977 | Benes et al. | 526/259 |
| 4,086,182 | 4/1978 | Hengelhaupt et al. | 252/182 |
| 4,500,601 | 2/1985 | Whitcomb | 528/392 |

FOREIGN PATENT DOCUMENTS

| | | |
|---|---|---|
| 2407306 | 9/1975 | Fed. Rep. of Germany . |
| 2407307 | 9/1975 | Fed. Rep. of Germany . |
| 2848967 | 11/1978 | Fed. Rep. of Germany . |
| 2849112 | 11/1978 | Fed. Rep. of Germany . |
| 77148599 | 5/1976 | Japan . |
| 77148600 | 5/1976 | Japan . |
| 78102400 | 5/1976 | Japan . |
| 77152934 | 6/1976 | Japan . |
| 78005238 | 7/1976 | Japan . |
| 78022598 | 8/1976 | Japan . |
| 78023399 | 8/1976 | Japan . |
| 80040711 | 9/1978 | Japan . |
| 709626 | 12/1977 | U.S.S.R. ........................... 546/271 |

OTHER PUBLICATIONS

E. Knowles and T. White, Adhesives and Resins, 2, 255 (1954), G.B. Pat. Spec. No. 1,230,220.
B. N. Kal'yan et al., Chem. Abs. 79, 80423j.
G. V. Dalipagich et al., Chem. Abs. 79, 80424k.
E. V. Zobov et al., Chem. Abs., 79, 93534w.
R. N. Faulkner, J. Oil Colour Chem. Assoc. 50, 524–44 (1967).
J. F. Kennedy et al., J. Chem. Soc. Perkin I, 488 (1973).
O. Vogl et al., J. Poly. Sci. Polym. Chem. Ed., 14 2725 (1976).
A. Winston et al., J. Polym. Sci. Che. Ed., 11, 597 (1978).
O. Vogl et al., J. Poly. Sci. Polym. Chem. Ed., 18 2755 (1980).
D. Braun and H. Boudevska, Eur. Polym. J., 12, 525 (1976).
V. Laurinavicius et al., Chem. Abs. 88, 106055.
L. I. Aristov et al., Chem. Abs., 71, 30337.
K. Idel et al., Makromol Chem. 177, 2927 (1976).
K. Kojima et al., Chem. Abs. 82, 17554.
K. Kojima et al., Chem. Abs. 83, 131987.
A. Winston et al., J. Polym. Sci. Chem. Ed. 13, 2019 (1975).
A. Winston et al., J. Polym. Sci. Chem. Ed. 14, 2155 (1976).
R. Paton et al., Aust. J. Chem. 27, 1185 (1974).

*Primary Examiner*—Thurman Page
*Assistant Examiner*—Peter F. Kulkosky
*Attorney, Agent, or Firm*—Gary L. Griswold; Walter N. Kirn; Lorraine R. Sherman

[57] ABSTRACT

Novel, linear, film-forming polymers and copolymers can be coated on certain metal surfaces, which polymers or copolymers are derived from one or more classes of ethylenically-unsaturated monomers and include at least one novel monomer having a bidentate chelating moiety. The polymers which contain bidentate chelating groups provide significant and varied chemical modification to a metal surface. When coated on a metal surface the polymers are useful as a protective coating or a priming layer.

13 Claims, No Drawings

BIDENTATE CHELATING MONOMERS AND POLYMERS

This is a continuation-in-part of application Ser. No. 527,333 filed Aug. 29, 1983 now abandoned.

TECHNICAL FIELD

The present invention relates to novel bidentate chelating monomers, their homopolymers, and their copolymers with non-chelating monomers. The polymers which contain bidentate chelating groups provide significant and varied chemical modification to a metal surface. When coated on a metal surface the polymers are useful as a protective coating or a priming layer.

BACKGROUND ART

Chelating agents are well known in the art, and are regarded in the art as compounds which contain two or more donor atoms selected from oxygen, nitrogen, and sulphur positioned so that they may react with a metal ion to form a five- or six-membered ring. The donor atoms may be of the same or different elements selected from the above group. Chelating agents having two or more atoms which can serve as donors are referred to as bidentate or polydentate groups. Oxygen-containing donor groups include alcohols, enols, phenols, ethers, carboxylic acids, and carbonyl groups, as in, for example, aldehydes, ketones, carboxylic esters, and carboxamides. Nitrogen-containing donor groups include imines and amines (primary, secondary and tertiary), including imines and amines in which the nitrogen atom forms part of a heterocyclic ring. Chelating agents, on reaction with many metal ions, form highly stable five- or six-membered rings.

Polymers containing chelating groups that react with metal surfaces are of interest in the present application. U.S. Pat. No. 3,395,134 discloses that

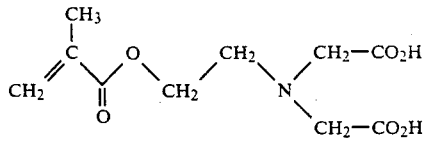

and related compounds, when copolymerized with methyl methacrylate to an incorporation of greater than 0.1 percent, impart much improved adhesion to steel. The synthesis of this compound has proved impossible to reproduce, which may be related to the fact that it is a zwitterionic chelating agent. It differs from chelating agents of the present invention in that it is a tridentate chelating agent.

Tannins have been incorporated in phenol-formaldehyde resins for use as anti-corrosion primers, as disclosed in E. Knowles and T. White, *Adhesives and Resins*, 2, 255 (1954). G. B. Patent Specification No. 1,230,220 relates to corrosion-preventing paints, which contain related chelating agents (i.e. polyhydroxy phenols) condensed with formaldehyde and cashew nut shell liquid. In these polymers, the chelating groups are not pendent to the main chain, as are required in the present invention.

Chelating groups have been incorporated into epoxy resins for adhesion to metal surfaces as disclosed in Japan Kokai 77-148,599, 77-148,600, 77-152,934, 78-05,238, 78-22,598, 78-23,399, 78-102,400; and B. N. Kal'yan et al. *Tr. Kishinev Politerkh Inst.* 97, (1971), G. V. Dalipagich et al. Ibid, 105, (1971), and E. V. Zobov et al. Ibid, 86, (1971). These polymeric resins which cross-link upon curing to three-dimensional structures are entirely different from the linear polymers of the present invention.

U.S. Pat. No. 3,304,276 teaches the modification of alkyd resins and drying oils so as to include polyhydric phenol groups (e.g., gallate) or acetoacetate groups. When applied to steel surfaces, they leach out Fe(III) ions, forming intermolecular chelate complexes. In R. N. Faulkner, *J. Oil Colour Chem. Assoc.* 50, 524–44 (1967), it is suggested that the good adhesion sometimes observed in these systems may result from coordination of gallate groups to metal ions without removal of the latter from the surface. These coatings contain oxygen in their backbone structures. Further, there is no teaching as to what materials and conditions would promote adhesion of resins to metal surfaces.

A mixture of chelating and non-chelating polymers as an anti-corrosion agent for iron or steel is disclosed in U.S. Pat. No. 4,086,182. The chelating polymers have, in addition to pendent chelating groups, pendent free acid groups on a hydrocarbon backbone.

U.S. Pat. No. 3,165,487 teaches a graft terpolymer of styrene-butadiene copolymer and a chelating alkali salt of vinylphenyl alpha-aminocarboxylic acid for which good adhesion to steel is claimed. This graft copolymer is unrelated to the random copolymers of the present invention.

U.S. Pat. No. 2,634,253 relates to the nitrile groups of a butadiene/methacrylonitrile/styrene terpolymer (10:2:1) which were reduced to amine groups and condensed with salicylaldehyde to give pendent Schiff-base groups. These chelating polymers extract metal ions from solution to give insoluble chelates which are in contrast to the polymers of the present invention which are soluble in many common organic solvents and are useful as layers coated on metal surfaces.

J. F. Kennedy, et al., *J. Chem. Soc. Perkin I*, 488 (1973) discloses homopolymers of 4- and 5-acrylamidosalicylic acid which have been used for selective binding of enzymes and proteins. Ger. Offen. 2,848,967 and Ger. Offen. 2,849,112 disclose salicylaldehyde derivatives, along with the corresponding Schiff bases obtained by condensation with amines, that form homopolymers and copolymers (1–99 percent) with conventional monomers, which are useful as molded articles, high-impact materials, coatings, adhesives, and treatments for paper and textiles.

Japan Kokai 80-40,711 teaches polymers containing pendent acetoacetate groups which are chelating groups for use as coatings on paper, fiber, and fabrics.

Chelating monomers are known in the art. Derivatives of salicylic acid have been disclosed by J. F. Kennedy et al. *J. Chem. Soc. Perkin I*, 488 (1973), O. Vogl et al. *J. Poly. Sci. Polym. Chem. Ed.* 14 2725 (1976), Ibid 18 2755 (1980), and D. Braun and H. Boudevska, *Eur. Polym. J.* 12, 525 (1976). Derivatives of 8-hydroxyquinoline are taught by V. Laurinavicius et al. *Chem. Abs.* 88, 106055, L. I. Aristov et al. *Chem. Abs.*, 71, 30337, K. Idel et al. *Makromol Chem.* 177, 2927 (1976), Ger. Offen. 2,407,306, and Cer. Offen. 2,407,307. Salicylaldehyde derivatives and salicylidene amine derivatives are disclosed in German Offen. 2,848,967 and German Offen. 2,849,112 respectively. Additional chelating monomers are disclosed in K. Kojima et al. *Chem. Abs.*

79, 87236, K. Kojima et al. *Chem. Abs.* 82, 17554, and K. Kojima et al. *Chem. Abs.* 83, 131987.

Polymers with chelating pendant hydroxamic acid groups or picolinic acid groups are disclosed in A. Winston et al. *J. Polym. Sci. Polym. Chem. Ed.* 13, 2019, (1975), Ibid 14, 2155 (1976), Ibid 11, 597 (1978), and R. Paton et al. *Aust. J. Chem.* 27, 1185 (1974).

SUMMARY OF THE INVENTION

The present invention provides novel, linear, film-forming polymers and copolymers which can be coated on certain metal surfaces, which polymers or copolymers are derived from one or more classes of ethylenically-unsaturated monomers and include at least one novel monomer having a bidentate chelating moiety. The polymers and copolymers have bidentate chelating moieties derived from the novel monomers of the invention. These novel monomers provide between 0.01 and 100 mole percent of the monomer units and preferably between 3 and 20 mole percent of the monomer units of the polymers and copolymers. The novel bidentate chelating monomers have structures having the formulae:

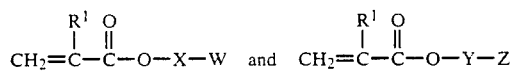

in which $R^1$ is H, lower alkyl, chlorinated lower alkyl, CN, or Cl and

X is an organic connecting linkage selected from a single bond and a branched or straight chain aliphatic group of up to 22 carbon atoms, providing that groups of 2 or more carbon atoms may be interrupted by one phenylene,

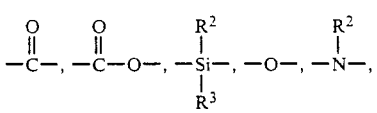

—S—, or —SO$_2$— moiety, wherein $R^2$, $R^3$ are independently H or lower alkyl ($C_1$ to $C_4$), providing that the total number of atoms found in the connecting linkage X is not more than 75, and providing that X does not react with W, nor enter into an chelating action, nor have polymerizing units within it;

W is a bidentate chelating moiety selected from the group consisting of

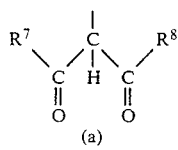

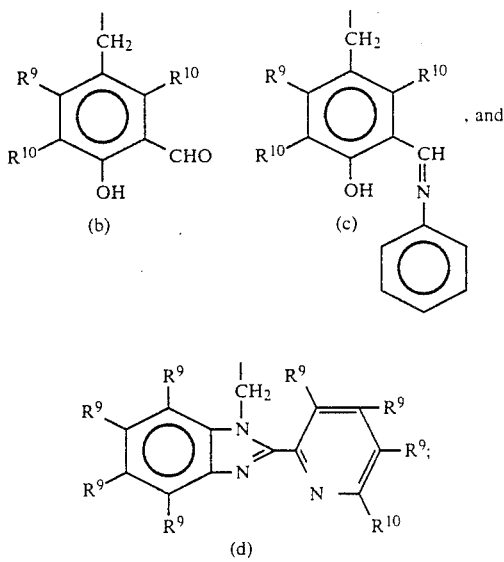

wherein $R^7$, $R^8$ are independently lower alkyl ($C_1$-$C_4$);

$R^9$ is independently selected from a hydrogen atom, a halogen atom, an NO$_2$ group, an alkyl group having 1 to 10 carbon atoms, an alkoxy group having 1 to 10 carbon atoms, an alkylthio group having 1 to 10 carbon atoms, a phenyl group, and a phenyl group substituted by up to 3 groups chosen from a halogen atom, an NO$_2$ group, and a lower alkyl group having 1 to 4 carbon atoms;

$R^{10}$ is independently selected from a hydrogen atom, a halogen atom, an NO$_2$ group, an alkyl group having 1 to 10 carbon atoms, an alkoxy group having 1 to 4 carbon atoms, an alkylthio group having 1 to 4 carbon atoms, and a phenyl group;

Y is an organic connecting linkage chosen from a single bond and the group —CH$_2$L- wherein L is a branched or straight chain aliphatic group of up to 21 carbon atoms that may be interrupted by up to one phenylene,

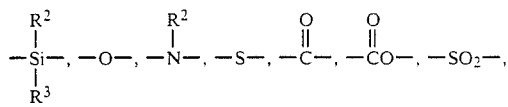

moiety for every group of two or more C atoms, wherein $R^2$, $R^3$ are independently H or lower alkyl ($C_1$-$C_4$), providing that the total number of atoms in the connecting linkage Y is not more than 75, and providing that Y does not react with Z, nor enter into any chelating action, nor have polymerizing units within it; and Z is a bidentate chelating moiety selected from the group consisting of

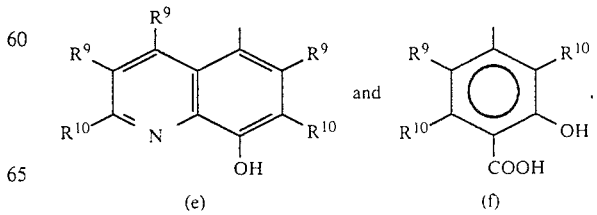

wherein $R^9$ and $R^{10}$ are as defined above.

The novel monomers of this invention may be prepared by condensation of equimolar amounts of a compound containing a bidentate chelating moiety with an acrylate-or methacrylate-group containing compound, one of which compounds has a reactive halogen atom, for example:

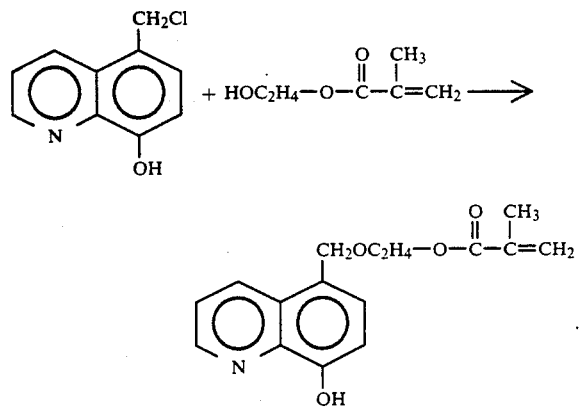

The polymers and copolymers of the present invention are film-forming and are highly adherent to metal surfaces, particularly such metals as Al, Mg, Zn, Fe, Cu, and their alloys. When coated on a metal surface to provide a composite structure, the polymeric coating provides a method of altering the properties of a metal surface in respect to corrosion, hydrophilicity and hydrophobicity, susceptibility to mechanical damage, light reflectance, and color, and is capable of conferring controlled adhesion properties at the free surface of the polymer layer. Such composite structures are disclosed in assignee's copending patent application U.S. Ser. No. 527,332, filed Aug. 29, 1983.

The polymers and copolymers of the present invention have linear, hydrocarbon backbones which may be substituted by halo or cyano moieties, said polymer or copolymer being derived from at least one ethylenically-unsaturated monofunctional monomer, at least one of which monomers contribute to the polymer or copolymer pendent bidentate chelating groups. There are no oxygen atoms within the backbone structure (i.e., the ethylenically-unsaturated portion of the polymer) and no crosslinks between the linear chains. The novel linear polymers and copolymers which have pendent bidentate chelating groups are of the non-graft and non-block type. It is not advantageous in many applications of the present invention to have a high concentration of chelating groups in the polymeric structure since such a polymer tends to sequester metal ions out of the metal surface and be non-adherent thereto.

The coatings of the present invention can be homopolymers of the bidentate chelating monomers, defined above or they can be copolymerized with ethylenically-unsaturated non-chelating monomers chosen to give to the resulting copolymer the properties required for suitable application to a metal surface and the properties suitable to the intended use of the treated metal surface. Thus, although homopolymers of the chelating monomers are useful, copolymers prepared from chelating and non-chelating monomers are generally more useful because of the extra dimension provided in the choice of the effect on the surface properties of the metal, and in the choice of application conditions of the polymer to the metal surface.

As used in the present invention:

"backbone" means in the main chain or spine of the polymer, exclusive of linking, and end-capping groups;

"chelating polymer" means any polymer in which from 0.01 to 100 percent of the repeat units have attached to them a pendent bidentate chelating group; the concentration of chelating groups and the identity of the co-monomers may be selected not only to provide good adhesion to the metal surface but also to provide maximum interaction with a subsequently applied topcoat; alternatively, they may be selected to repel surface contaminants;

"copolymer" means any polymer having a structural arrangement of two or more different monomers in random sequence;

"alloy" means a mixture of a metal with one or more other metal or non-metallic elements such as nickel, chromium, copper, and carbon (e.g., brass, bronze, chrome-nickels, steels, carbon steel); and "lower alkyl" means an alkyl group having 1 to 4 carbon atoms.

The film-forming polymers and copolymers of the present invention have pendent bidentate chelating groups. They are linear polymers which are not cross-linked. Hence, epoxy materials which promote oxygen-containing crosslinking bridges are not included in the present invention. The present invention relates to homopolymers and random copolymers. Graft copolymers and physical mixtures of chelating and non-chelating polymers have disadvantages in their physical properties, the former having high chelating strength which tends to promote the sequestering (solvation) of metal ions from the surface and is deleterious to adhesion, whereas the latter leads to variable and inconsistent adhesive properties.

The present invention teaches the value of the disclosed bidentate chelating moieties in their film-forming polymers because of their moderate chelating strength. It is important that the localized chelating strength be within the correct range. If it is too low, little more adhesion to the metal surface occurs than with a simple hydrocarbon polymer; if it is too high metal atoms are pulled from the surface to make a permanent complex with the chelate. Tridentate and higher chelates are generally unsuitable because of solvation of the metal surface.

Thus, the bidentate chelate-containing polymers of this invention are surprisingly tolerant of the molar ratio of that moiety to the other monomer moieties, and of the choice of the other ethylenically-unsaturated monomers. This provides wide freedom in the selection of polymers to suit the metal surface, and at the same time allows a wide range in the intended use of the treated surface, with latitude remaining in the conditions for the application of the polymers to the metal.

DETAILED DESCRIPTION

The present invention provides novel bidentate chelating monomers having ethylenically-unsaturated moieties, their homopolymers, and their copolymers with non-chelating monomers. When coated on a metal surface, the homopolymers and copolymers of the invention provide a composite structure. Polymers of the invention have at least one structural unit selected from the group consisting of

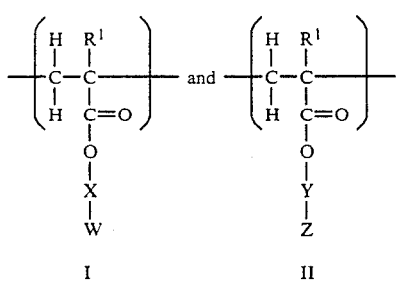

wherein $R^1$ is hydrogen, lower alkyl, chlorinated lower alkyl, CN, or Cl;

X is an organic connecting linkage selected from a single bond and a branched or straight-chain aliphatic group of up to 22 carbon atoms long, providing that groups of 2 or more carbon atoms may be interrupted by phenylene,

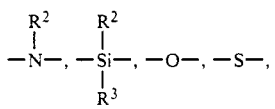

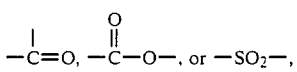

wherein $R^2$, $R^3$ are independently H or lower alkyl ($C_1$ to $C_4$), providing that the total number of atoms in the connecting linkage X is not more than 75, and providing that X does not react with W, nor enter into any chelating action, nor have polymerizing units within it; and Y is an organic connecting linkage selected from a single bond and the group —$CH_2L$—, wherein L is a branched or straight chain aliphatic group of up to 21 carbon atoms long, providing that groups of two or more carbon atoms may be interrupted by up to one phenylene,

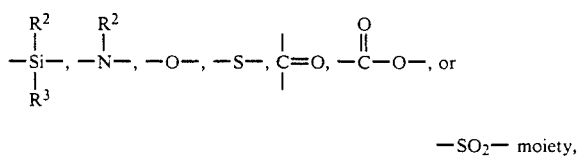

—$SO_2$— moiety, wherein $R^2$, $R^3$ are H or lower alkyl ($C_1$ to $C_4$), providing that the total number of atoms in the connecting linkage Y is not more than 75, and providing that Y does not react with Z, nor enter into any chelating action, nor have polymerizing units within it; and W is a bidentate chelating moiety selected from the group

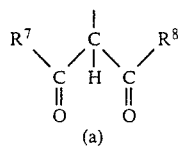

-continued

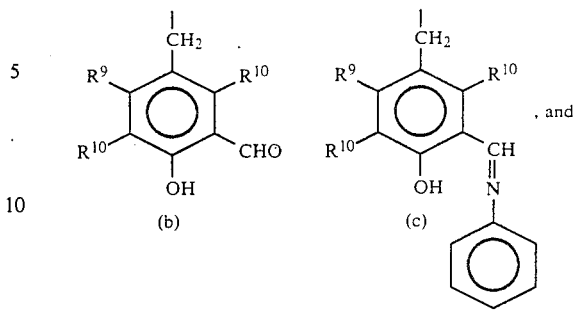

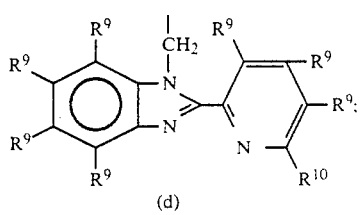

wherein $R^7$, $R^8$, and independently lower alkyl ($C_1$-$C_4$), $R^9$ is independently selected from a hydrogen atom, a halogen atom selected from fluorine, chlorine, bromine and iodine, an $NO_2$ group, an alkyl group having 1 to 10 carbon atoms, an alkoxy group having 1 to 10 carbon atoms, an alkylthio group having 1 to 10 carbon atoms, a phenyl group, and a phenyl group substituted with up to 3 groups chosen from a halogen atom, an $NO_2$ group, and a lower alkyl group having 1 to 4 carbon atoms, and $R^{10}$ is independently selected from a hydrogen atom, a halogen atom selected from fluorine, chlorine and bromine, an $NO_2$ group, an alkyl group having 1 to 10 carbon atoms, an alkoxy group having 1 to 4 carbon atoms, an alkylthio group having 1 to 4 carbon atoms, and a phenyl group;

Z is a bidentate chelating moiety selected from the group consisting of

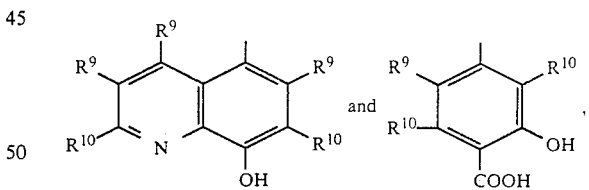

wherein $R^9$ and $R^{10}$ are as defined above.

The polymers comprise chains of structural units totalling 50 to 10,000 in number.

The metal surface comprises metal atoms and ions selected from 1) the transition metals and 2) the metals of Groups IIA, IIIA, and IVA of the Periodic Table or alloys thereof. The coated linear, film-forming polymer or random copolymer has a hydrocarbon backbone which may be substituted by halogen or cyano moieties, said polymer or copolymer being derived from at least one ethylenically-unsaturated monofunctional monomer, at least one of which monomers contributes to the polymer or copolymer pendent bidentate chelating groups whose chelating ability is less than that required for dissolution of metal ions from said metal surface.

The organic polymeric coating of the present invention in which the bidentate chelating group can form a complex compound with a metal, comprises:

1) 0.01 to 100 mole percent, and preferably 3 to 20 mole percent, of at least one chelating monomer unit selected from units having the formulae

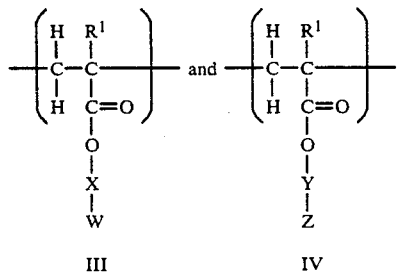

wherein $R^1$, X, W, Y, and Z are as defined above, and 2) 99.99 to 0 mole percent, and preferably 97 to 80 mole percent of units derived from copolymerizable ethylenically-unsaturated monomers, which monomers provide hydrocarbon backbones, optionally substituted by CN, Cl, lower alkyl, chlorinated lower alkyl, or fluorocarbon-containing moieties, to the resulting copolymer.

The molecular weight of polymers is in the range of 5,000 to 1,000,000.

Preferably the chelating monomers conform to one of the general structures

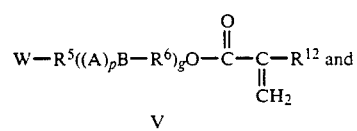

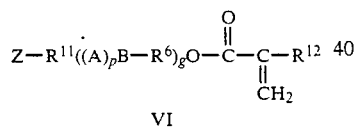

which provide preferred chelating monomer units having one of the general structures

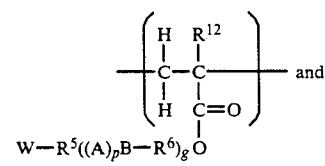

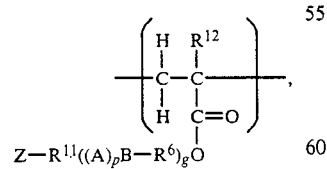

wherein

A is 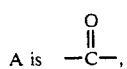

or $-SO_2-$.

B is a single bond, $-O-$, $-S-$, $-NR^2-$, $-SiR^2R^3-$, or phenylene, wherein $R^2$ is H or lower alkyl ($C_1$ to $C_4$), and wherein $R^3$ is H or lower alkyl ($C_1$ to $C_4$) independently of $R^2$, $R^{11}$ is a single bond or $-(CH_2)_{1-g}R^6$, wherein g and $R^6$ are as defined below, $R^6$ is an alkylene group having 1 to 10 carbon atoms, or an alkylene group having 1 to 10 carbon atoms which is substituted with up to 3 alkyl groups having 1 to 4 carbon atoms, $R^5$ is a single bond or the group defined for $R^6$, $R^{12}$ is hydrogen or a methyl group, p is an integer having a value of 0 or 1, g is an integer having a value of 0 or 1, and wherein W and Z are as defined above; and with the proviso that when B is $-S-$, A can only be

Examples of novel chelating monomers which are suitable for use in the invention and conform to Formulae V and VI include those having the structures (1) to (6).

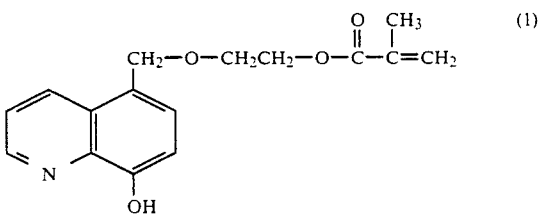

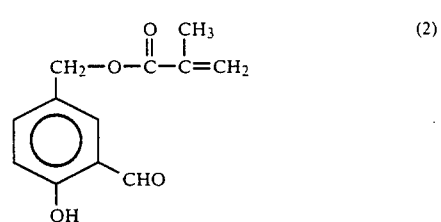

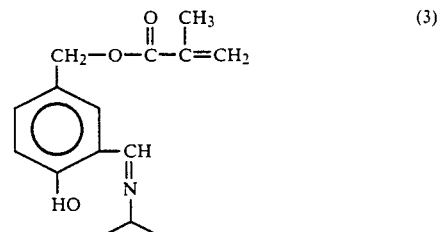

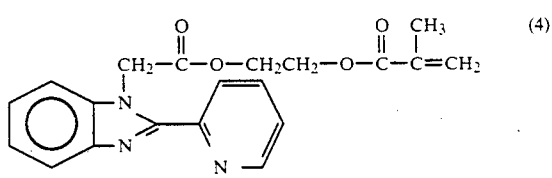

-continued
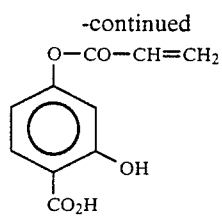
(5)
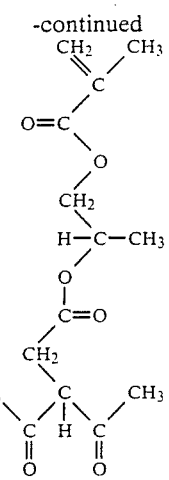
(6)
Other examples of monomers falling within formulae V and VI include;
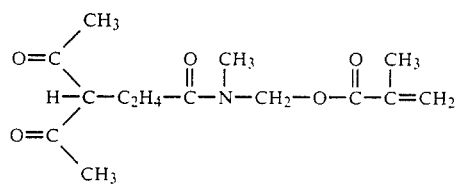
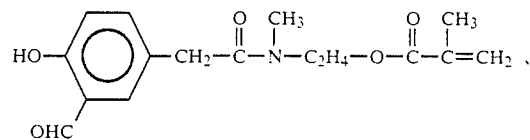
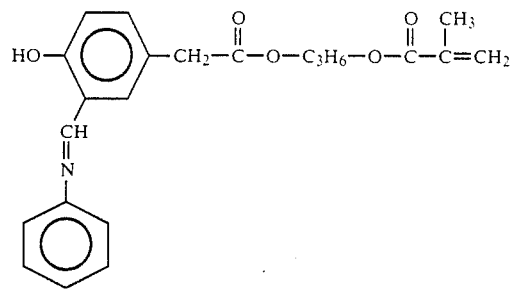
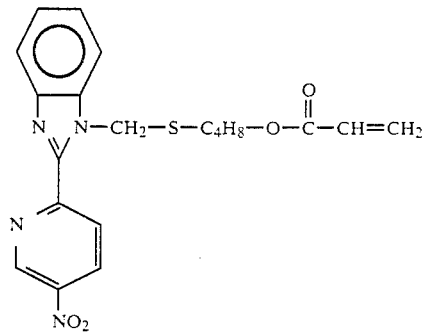

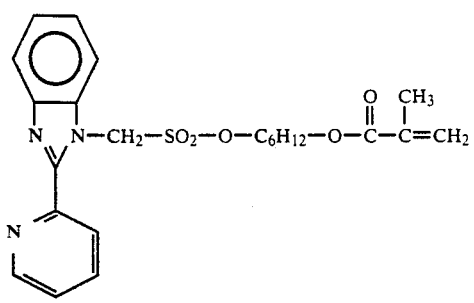
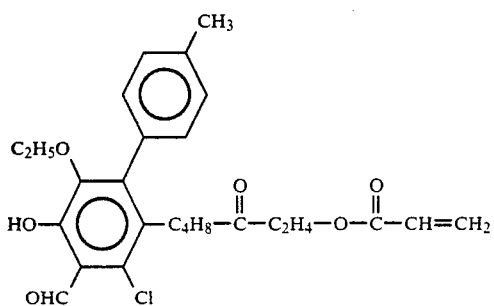
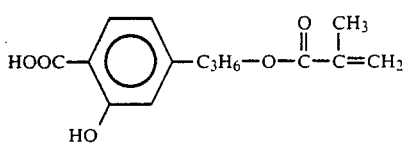
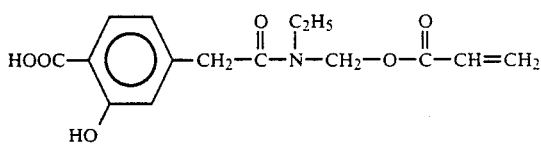
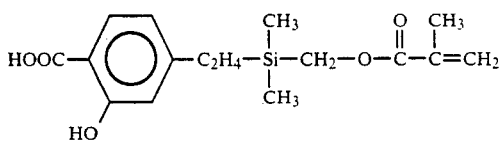
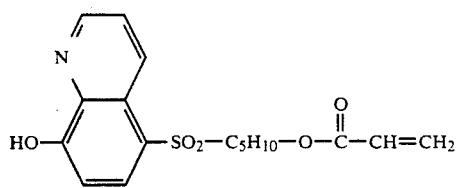
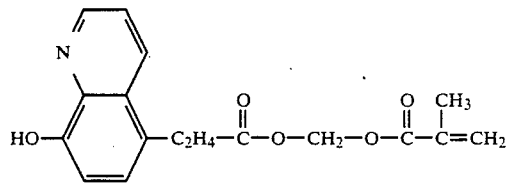
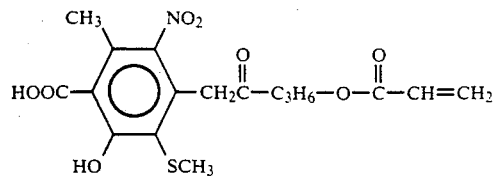

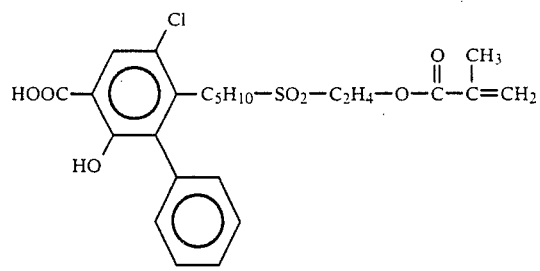
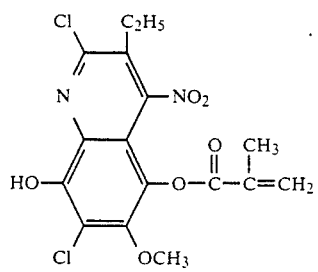
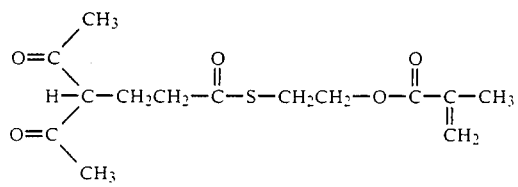
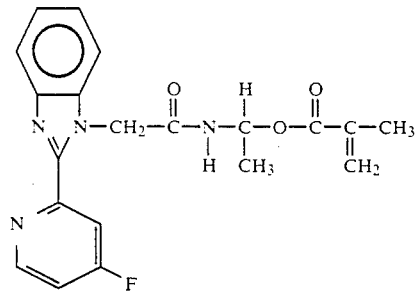
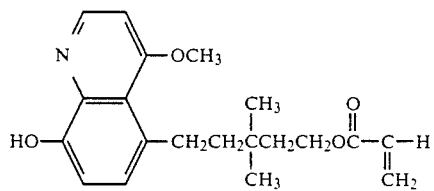
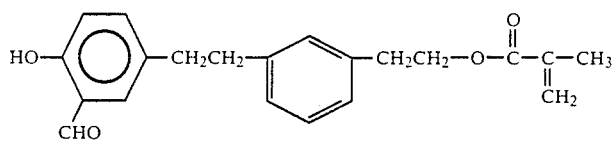
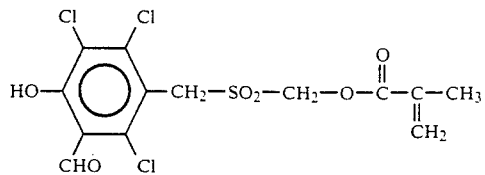

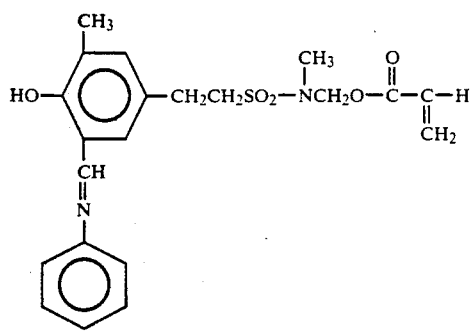

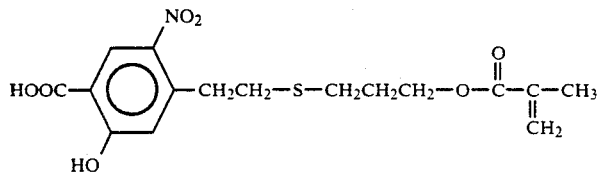

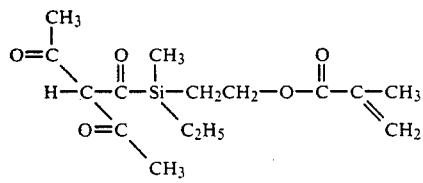

The metals with which these polymers can form strongly adhesive bonds are transition metals of the Periodic Table and the metals of Groups IIA, IIIA, and IVA and alloys thereof, such as aluminum, magnesium, zinc, iron, copper, brass, etc. The metal may be self-supporting, a thin layer on a support, or in a finely divided particle form.

The non-chelating monomers which can be copolymerized with the chelating monomers may be selected from any conventional monomer having ethylenic unsaturation, such as ethylene, tetrafluoroethylene, and other olefins, vinyl alcohol and its esters, dienes including butadiene, vinyl halides, for example vinyl bromide, vinyl chloride and vinyl fluoride, vinylidenes, for example vinylidene chloride, nitriles of $\alpha,\beta$-unsaturated acids, for example acrylonitrile or methacrylonitrile, $\alpha,\beta$-unsaturated acids and their esters or halogen derivatives, for example acrylic acid, methacrylic acid, crotonic acid, maleic acid, itaconic acid, methyl methacrylate, ethyl acrylate, propyl acrylate, butyl acrylate, octyl acrylate, dimethyl maleate, 2-ethyl-hexyl acrylate, ethyl methacrylate, isopropyl methacrylate, dimethylaminoethyl methacrylate, diethylaminoethyl acrylate, glycidyl methacrylate, glycidyl acrylate or chloromethyl methacrylate, $\alpha,\beta$-unsaturated carboxylic acid amides and their derivatives, for example acrylamide and methacrylamide, aromatic vinyl compounds, for example styrene, methylstyrene, vinyltoluene or $\alpha$-chlorostyrene, vinyl ketones, for example methyl vinyl ketone, vinyl esters, for example vinyl acetate, heterocyclic vinyl compounds, for example vinylpyridine and N-vinylpyrrolidone, N-vinylcarbazole, vinyl ethers and compounds which have olefinic double bonds. The choice of these monomers depends on the properties required of the resulting copolymers. The inclusion of fluorocarbon substituents in the monomers can have advantageous effects on the surface properties as is well known in the art. A discussion of this range of monomers and their copolymerization properties may be found in "Textbook of Polymer Chemistry", F. W. Billmeyer, Interscience Publishers, Inc., N.Y. (1957), Chap. 29, 30, 33 through 38, and, "Monomers", E. R. Blout and H. Mark, Interscience Publishers, Inc., N.Y. (1951), and "Copolymerization", T. Alfrey, Jr., J. J. Bohner, H. Mark, Interscience Publishers, Inc., N.Y. (1964).

The copolymers are characterized in that they contain at least one non-chelating organic monomer such as vinyl or vinylidene monomers, methyl methacrylate, butyl acrylate, styrene (see for example the listing in U.S. Pat. No. 3,395,134, column 7, lines 60-75, which is incorporated herein by reference), and at least one pendent chelate monomer of the invention, such that the conventional organic monomers are incorporated in a total amount from 0 to 99.99, preferably 80 to 97, mole percent and the pendent chelate monomers in a total amount of 0.01 to 100, preferably 3 to 20, mole percent of the polymer, and the nonchelating monomer and chelating monomer moieties are distributed randomly within the copolymer.

For attachment to a metal surface, copolymers of the invention are much preferred over homopolymers of the chelating monomers. These are random copolymers and do not include block copolymers.

By having chelating sites spaced apart within the polymer as is the case in a random copolymer, there is a reduced tendency to leach metal ions from any metal surface and adhesion is thereby improved. Homopolymers of the chelating monomers would be less likely to possess useful physical properties and, therefore, provide a more restricted choice for a particular application. By incorporating the chelating monomers at low levels in conventional polymers, the useful properties of the latter may be combined with improved adhesion. Generally, it is expected that levels of incorporation of the chelating monomers within the copolymer of from 0.01 to 20 percent on a molar basis would be the most useful. The polymers as prepared do not contain metal ions.

While a variety of chelating groups may be incorporated in any polymer, it should be understood that only a limited range of chelating groups will be suitable for a given metal surface. Hence, it is necessary to select the chelating group(s) to be present in the polymer in order to attain the optimum properties for any particular application.

The polymers and copolymers of this invention can be prepared as is known in the art in mass, in solution, in suspension, and emulsion systems, using the accepted initiating systems, such as by using the peroxy compounds that generate radicals, e.g., potassium persulfate, or thermally, or with ultraviolet light, or with ionizing radiation, and in some cases, with ionic catalysts, both cationic and anionic, e.g. $BF_3$, sodium amide, HF, etc.

Copolymers of the invention when applied to metal surfaces have shown much increased adhesion to the metal surface compared with polymers not containing pendent chelating groups. Shear strength improvements of 300 percent have been found.

Improved adhesion is thought to result from chemical reaction of the pendent chelating agents on the polymer with metal ions at the surface of the metal resulting in the formation of covalent bonds between the polymer and the metal. These bonds are formed rapidly, and are stable towards hydrolysis.

When the polymers of the invention are coated on a metal surface the resulting composite structures are useful in varied applications including the following:

a) as a highly adhesive thin layer providing protection of metal against corrosion b) as a priming layer with enhanced adhesive properties for subsequent lacquer or paint application c) as a highly adhesive layer showing release properties at its exposed surface, e.g., for contaminants or corrosive materials d) as layers widely ranging in physical properties, e.g., as hard brittle layers to tough flexible layers (depending on the copolymer chosen).

Objects and advantages of this invention are further illustrated by the following examples, but the particular materials and amounts thereof recited in these examples, as well as other conditions and details, should not be construed to unduly limit this invention.

Six novel monomers, illustrated earlier by structures 1) to 6), were synthesized as follows:

EXAMPLE 1

5-(Methacryloyloxyethoxymethyl)-8-hydroxyquinoline (compound 1 above)

5-Chloromethyl-8-hydroxyquinoline (46 g) (prepared by the method of Kolobielski, *J. Heterocyclic Chem.* 275, (1966)), sodium acetate (16.4 g) and hydroxyethyl methacrylate (200 ml) were stirred and heated on a steam bath for 5 hours, and the resulting slurry was dissolved in water (1 litre). Solid sodium carbonate was added until alkaline, and then the precipitate was collected, washed with water, dissolved in ether (500 ml), dried with $MgSO_4$, and then treated with HCl gas to precipitate the hydrochloride salt. The latter was collected, washed with ether, air dried on the filter, dissolved in water (1 litre), and treated with solid sodium carbonate until alkaline. The resulting precipitate was collected, washed with water, dried, and crystallized from light petroleum (b.p. 60°–80° C.) to give 23 g colorless needles, m.p. 90°–1° C.

Spectroscopic analysis confirmed the identity of the product to be the compound 5-(methacryloyloxy-ethoxymethyl)-8-hydroxyquinoline.

EXAMPLE 2

5-(Methacryloyloxymethyl) salicylaldehyde (compound 2 above)

5-Chloromethylsalicylaldehyde (34 g) (prepared by the method of Angyal et al., *J. Chem. Soc.* 2141, (1950)) was added to a stirred mixture of acetone (250 ml), sodium hydrogen carbonate (33.6 g), and methacrylic acid (34.4 g)

and the mixture was stirred under reflux for 2½ hours. Addition of the mixture to ice water gave a grey precipitate which was collected, washed with water, dried, and crystallized from light petroleum (b.p. 60°–80° C.). Yield 32.1 g, m.p. 82°–4° C.

Elemental and spectroscopic analysis confirmed /-> the product to be the compound 5-(methacryloxymethyl)-salicylaldehyde.

EXAMPLE 3

5-(Methacryloyloxymethyl) salicylideneaniline (compound 3 above)

The compound of Formula (2) (19.35 g), aniline (8.19 g), and toluene (200 ml) were refluxed with azeotropic removal of water for 2½ hours. The cooled solution was evaporated under reduced pressure, and the residual oil adsorbed on silica gel (90 g . The mixture was extracted al room temperature with successive portions of light petroleum until no more color was extracted.

Evaporation of the combined extracts left a yellow oil which slowly solidified on storage in the refrigerator. It gave identical spectra to a sample of the crude product which was purified by column chromatography on silica gel (eluant ether/light petroleum 1:1).

Spectroscopic analysis confirmed the product as the compound 5-(methacryloyloxymethyl) salicylideneaniline.

EXAMPLE 4

1-(Methacryloyloxyethyoxycarbonylmethyl)-2-(2'-pyridyl)benzimidazole (compound 4 above)

2-(2-Pyridyl)benzimidazole (11.7 g) in N,N-dimethylformamide (150 ml) was treated with sodium hydride (3.9 g, 50 percent dispersion), with stirring and ice-bath cooling. After effervescence had subsided, chloroacetoxyethyl methacrylate (15 g) (prepared as in *Chem. Abs.* 68, 105913 g) was added and the temperature was then raised to 70° C. for one hour. After cooling, addition of the mixture to ice water produced a viscous oil which was extracted into ether and isolated by evaporation. The crude product was dissolved in 2N HCl, then extracted with ether (2×100 ml) (extracts discarded), and then aqueous layer was made alkaline with 2N NaOH, and then the product was re-extracted with ether (3×100 ml). Evaporation of washed ($H_2O$) and dried ($MgSO_4$) ether layers left a brown, viscous gum.

An analytical sample was chromatographed on a column of neutral alumina (eluent ether), while the bulk was slurried with 35 g alumina in 200 ml ether, filtered, the residue washed well with ether, and the ether solution evaporated, to give a colorless gum, which solidified slowly on storage in the refrigerator.

Elemental and spectroscopic analysis confirmed the product to be the compound 1-(methacryloyloxyethyoxy-carbonylmethyl)2-(2'-pyridyl)- benzimidazole.

EXAMPLE 5

4-Acryloyloxysalicylic Acid (compound 5 above)

2,4-Dihydroxybenzoic acid (77 g), sodium hydroxide (20 g) and sodium tetraborate (68 g) were dissolved in water (200 ml), then treated further with 20 g sodium hydroxide in water (200 ml). The resulting dark solution was stirred vigorously and the temperature was maintained at 20°-25° C. while acryloyl chloride (50 ml) was added dropwise. After one hour's stirring at room temperature, acidification with concentrated HCl gave a white precipitate, which was collected, washed with water, and dried in vacuo. Crystallization from either dilute acetic acid or acetone/toluene gave a buff powder, m.p. 141°-3° C. Yield 34 g. The product gave a purple color with $FeCl_3$, indicating the salicylic acid function to be intact. Spectroscopic analysis confirmed the product to be the compound 4-acryloyloxysalicylic acid.

EXAMPLE 6

3-(Methacryloyloxyprop-2'-oxycarbonylmethyl)pentane-2,4-dione (compound 6 above)

Chloroacetoxypropyl methacrylate (CAPM) was prepared by condensation of chloroacetyl chloride with hydroxypropyl methacrylate in pyridine (cf Chem. Abs. 68, 105913 g) b.p. 92°-4° C./0.2mm.

CAPM (44 g , acetylacetone (40 g , anhydrous $K_2CO_3$ (32 g), and acetone (200 ml) were stirred under reflux for 19 hours. The cooled mixture was filtered, the residue was washed well with acetone, and the combined filtrate and washings were evaporated under reduced pressure. Distillation of the residual oil gave a fore-run of unreacted starting materials, followed by 27.9 g product, b.p. 130°-2° C./0.1 mm.

Spectroscopic analysis confirmed the product to be the compound 3-(methacryloyloxyprop-2'-oxycarbonylmethyl)-pentane-2,4-dione; polymerization of the monomer to give a novel polymer is described in EXAMPLE 13.

The above-described novel monomers were copolymerized as described in Examples 7-12.

EXAMPLES 7-12

Emulsion copolymers of compounds (1)-(6)

The desired amount of chelating monomer (see EXAMPLE 14 for relative amounts used) was dissolved in 30 g of a 4:1 (v/v) mixture of methyl methacrylate and butyl acrylate, and this solution was added to 70 ml 4 percent (w/v) sodium lauryl sulphate solution containing 0.03 g potassium persulphate. This mixture was stirred 1 hour at room temperature under $N_2$, and then it was stirred two hours at 70° C. under $N_2$. The polymer was coagulated by pouring into methanol, collected, dissolved in acetone, re-precipitated with methanol, and dried at 45° C. under reduced pressure. Data relating to the chelating polymers is shown in TABLE I of EXAMPLE 14.

EXAMPLE 13

Homopolymerization of the chelating monomers of EXAMPLES 1-6 were carried out. Only the compound of Formula (1) failed to give any polymer, while the compound of Formula (3) gave only low molecular weight, non-film-forming material; the compounds of Formulas (2), (4), and (5) were successfully polymerized in solution, and the compound of Formula (6), being a liquid, gave an emulsion polymer.

EXAMPLE 14

Analysis of the Chelating Polymers

Incorporation of the chelating groups in the polymer was monitored by UY spectrometry. Each of the monomers (1) to (6) showed a characteristic, intense absorption in the wavelength range 280 to 350 nm, in which the methyl methacrylate/butyl acrylate copolymer was transparent. The UV spectra of the product polymers were therefore used to give both a qualitative and quantitative measure of the incorporation of the chelating groups, and this was found to match closely their incorporation in the monomer feed (Table 1). In addition, $^{13}C$ NMR spectra were recorded for copolymers containing compounds (1) and (3). These clearly showed the signals associated with the aromatic carbons in the chelating groups.

TABLE 1

| Monomer | Mole % in Feed | Mole % in Polymer |
| --- | --- | --- |
| (1) | 1.0 | 1.4 |
|  | 3.0 | 4.4 |
|  | 5.0 | 7.2 |
|  | 7.5 | 9.5 |
|  | 10.0 | 15.5 |
|  | *30.0 | 30.7 |
| (2) | 1.0 | no data |
|  | 3.0 | 4.0 |
|  | 5.0 | 6.8 |
| (3) | 1.0 | 0.8 |
|  | 3.0 | 2.3 |
|  | 5.0 | 11.4 |
| (4) | 1.0 | 1.4 |
|  | 3.0 | 2.9 |
|  | 5.0 | 3.1 |
| (5) | 1.0 | 2.4 |
|  | 3.0 | 3.3 |
|  | 5.0 | 5.1 |
|  | 7.5 | 6.6 |
|  | 10.0 | 9.5 |
|  | 1.0 | 1.2 |
|  | 3.0 | 2.7 |
| (6) | 5.0 | 7.5 |
|  | 7.5 | 6.0 |
|  | 10.0 | 8.6 |
|  | 15.0 | 26.2 |

*solution polymer.

The following examples illustrate the improved adhesion to mild steel panels of lacquer-type coatings.

EXAMPLE 15

Metal surface preparation

Mild steel sheet (20 gauge) was subjected to a degrease-abrade-degrease routine immediately before use. After wiping with acetone-soaked tissue, it was abraded with Scotch TM brand (3M) fine-grade discs in a hand-held rotary sander, then hand-finished with 400 grit paper. The final step was degreasing in a trichloroethylene vapor bath.

Coatings

Coatings were made on the prepared steel sheet from 6 percent w/v solutions of polymer in acetone or chloroform. A variety of techniques were used, including wire wound bars, blade and flood-coating, giving thicknesses in the range of 2 to 10 micrometers. Coating thickness was monitored by an Elcometer 150N eddy current tester (Elcometer Instruments Ltd., Manchester, England).

Adhesion to Metals

Coatings of copolymers of EXAMPLES 7-12 were tested with chelating group incorporations (nominal) of 1, 3 and 5 mole percent. Adhesion of the coatings was monitored by a cross-hatch tape test (ASTM D3359-74). Whereas, the reference copolymer of MMA and BA failed this test completely, all the chelating polymers examined passed undamaged, showing that substantial improvements in adhesion were provided by this technique. Even when a tape of double the specified peel strength was used, the coatings still survived intact.

EXAMPLE 16

An evaluation of resins of the invention cured under pressure was conducted. Lap joints were made between steel strips, and the shear strengths recorded. The steel strips were prepared as in EXAMPLE 15 and an Instron brand tensiometer was used to measure the shear strengths.

Using the formulation listed below, and an overlap area of 18 mm × 18 mm, lap shear strengths of approx. 50 kg were obtained, with a reproducibility of approximately 10 percent.

| | |
|---|---|
| Poly(MMA) in MMA (4 percent w/w) | 4 parts |
| Tetraethyleneglycol dimethacrylate | 6 parts |
| Benzoyl peroxide | 0.1 part |
| N,N-dimethylaniline | 0.1 part |

Chelating groups were introduced by replacing 10 weight percent of the MMA with chelating monomer, giving the results listed in Table 2.

TABLE 2

| Chelating Monomer | Shear Strength (kg) |
|---|---|
| (5) | 91 |
| (1) | 94 |
| (2) | 64 |
| (4) | 47 |
| none | 50 |

Thus, it was established that chelating monomers could provide significant improvements in adhesive strength for 100 percent solids systems, with salicylic acid and 8-hydroxyquinoline showing the greatest effect. However, the concentration of chelating groups could not be varied over a wide range because of the limited solubility of the chelating monomers in methyl methacrylate.

Various modifications and alterations of this invention will become apparent to those skilled in the art without departing from the scope and spirit of this invention, and it should be understood that this invention is not to be unduly limited to the illustrative embodiments set forth herein.

We claim:

1. A compound having a formula selected from:

$$CH_2=C(R^1)-C(O)-O-X-W \text{ and } CH_2=C(R^1)-C(O)-O-Y-Z$$

wherein $R^1$ is H, lower alkyl, chlorinated lower alkyl, CN, or Cl;

X is an organic connecting linkage selected from a single bond and a branched or straight chain aliphatic group of up to 22 carbon atoms, providing that groups of two or more carbon atoms may be interrupted by one phenylene, $$-N(R^2)-, -O-, -S-, -C(=O)-,$$

$$-C(O)-O-, -SO_2-, \text{ or } -Si(R^2)(R^3)-$$

moiety, wherein $R^2$ and $R^3$ are independently H or lower alkyl having 1 to 4 carbon atoms, provided that the total number of atoms of connecting linkage X is not more than 75, and providing that X does not react with W, nor enter into any chelating action, nor have polymerizing units within it; and W is a bidentate chelating moiety selected from the group consisting of (a) $R^7$, $R^8$ substituted on a CH with two C=O groups (acetylacetonate-type)

(b) a benzene ring with $CH_2$, $R^9$, $R^{10}$, OH, CHO substituents (c) a benzene ring with $CH_2$, $R^9$, $R^{10}$, OH, CH=N-phenyl substituents, and (d) a benzimidazole/pyridine system with $CH_2$, $R^9$, $R^{10}$ substituents wherein $R^7$, $R^8$ are independently lower alkyl ($C_1$-$C_4$);

$R^9$ is independently selected from a hydrogen atom, a halogen atom selected from fluorine, chlorine, bromine and iodine, an $NO_2$ group, an alkyl group having 1 to 10 carbon atoms, an alkoxy group having 1 to 10 carbon atoms, an alkylthio group having 1 to 10 carbon atoms, a phenyl group, and a phenyl group substituted with up to 3 groups chosen from a halogen atom, an $NO_2$ group, and a lower alkyl group having 1 to 4 carbon atoms;

$R^{10}$ is independently selected from a hydrogen atom, a halogen atom selected from fluorine, chlorine and bromine, an $NO_2$ group, an alkyl group having 1 to 10 carbon atoms, an alkoxy group having 1 to 4 carbon atoms, an alkylthio group having 1 to 4 carbon atoms, and a phenyl group;

Y is an organic connecting linkage chosen from a single bond and the group —CH$_2$L— where L is a branched or straight chain aliphatic group of up to 21 carbon atoms, providing that groups of two or more carbon atoms may be interrupted by up to one phenylene, $$-\underset{\underset{R^3}{|}}{\overset{\overset{R^2}{|}}{Si}}-, -O-, -\underset{}{\overset{\overset{R^2}{|}}{N}}-, -S-, -\overset{\overset{O}{||}}{C}-, -\overset{\overset{O}{||}}{C}-O-, \text{ or } -SO_2-$$

moiety for every group of two or more C atoms, wherein R$^2$ and R$^3$ are independently H or lower alkyl or 1 to 4 carbon atoms, providing that the total number of atoms of connecting linkage Y is not more than 75, and providing that Y does not react with Z, nor enter into any chelating action, nor have polymerizing units within it; and Z is a bidentate chelating moiety selected from the group consisting of (e) and (f) [quinolinol and hydroxybenzoic acid structures with R$^9$ and R$^{10}$ substituents]

wherein R$^9$ and R$^{10}$ are as defined above.

2. A compound having a formula selected from $$W-R^5((A)_pB-R^6)_gO-\overset{\overset{O}{||}}{C}-\underset{\underset{CH_2}{||}}{C}-R^{12}$$

and $$Z-R^{11}((A)_pB-R^6)_gO-\overset{\overset{O}{||}}{C}-\underset{\underset{CH_2}{||}}{C}-R^{12}$$

wherein

A is $-\overset{\overset{O}{||}}{C}-$,

B is a single bond, —O—, —S—, —NR$^2$—, or phenylene, wherein R$^2$ is H or lower alkyl, and wherein R$^3$ is H or lower alkyl independently or R$^2$;

R$^6$ is an alkylene group having 1 to 10 carbon atoms, or an alkylene group having 1 to 10 carbon atoms which is substituted with up to 3 alkyl groups having 1 to 4 carbon atoms;

R$^5$ is a single bond or R$^6$;

R$^{12}$ is hydrogen or a methyl group;

p is an integer having a value of 0 or 1;

g is an integer having a value of 0 or 1; and

W is a bidentate chelating moiety selected from the group consisting of (a) [structure with R$^7$, R$^8$, CH, and two C=O groups]

(b) [phenol structure with CH$_2$, CHO, OH, R$^9$, R$^{10}$ substituents]

(c) [phenol structure with CH$_2$, CH=N-phenyl, OH, R$^9$, R$^{10}$ substituents], and (d) [benzimidazole-pyridine structure with CH$_2$ linker and R$^9$, R$^{10}$ substituents]

wherein

R$^7$ and R$^8$ are independently a lower alkyl group having 1 to 4 carbon atoms; and R$^9$ is independently selected from a hydrogen atom, a halogen atom selected from fluorine, chlorine, bromine, and iodine, an NO$_2$ group, an alkyl group having 1 to 10 carbon atoms, an alkoxy group having 1 to 10 carbon atoms, a phenyl group, and a phenyl substituted with groups chosen from a halogen atom, an NO$_2$ group, and a lower alkyl group having 1 to 4 carbon atoms; and R$^{10}$ is independently selected from a hydrogen atom, a halogen atom selected from fluorine, chlorine and bromine, an NO$_2$ group, an alkyl group having 1 to 10 carbon atoms, an alkoxy group having 1 to 4 carbon atoms, an alkylthio group having 1 to 4 carbon atoms, and a phenyl group;

R$^{11}$ is a single bond or —(CH$_2$)$_{1-g}$R$^6$—, wherein g and R$^6$ are as defined above; and Z is a bidentate chelating moiety selected from the group

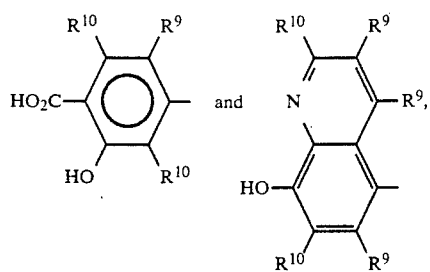

wherein $R^9$ and $R^{10}$ are as defined above.

3. A compound selected from the group consisting of:

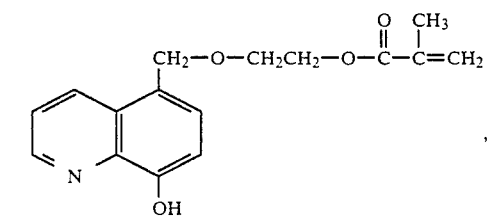

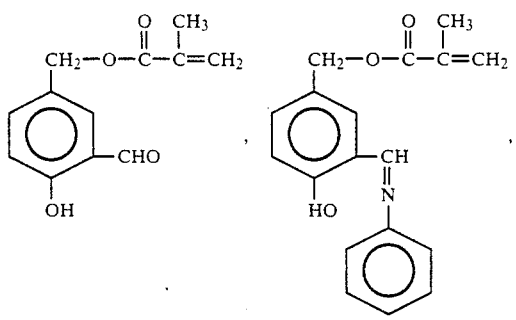

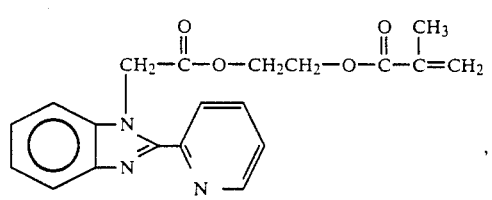

4. The compound according to claim 2 selected from the group consisting of:

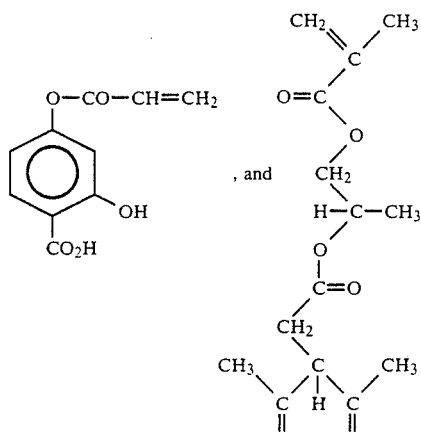

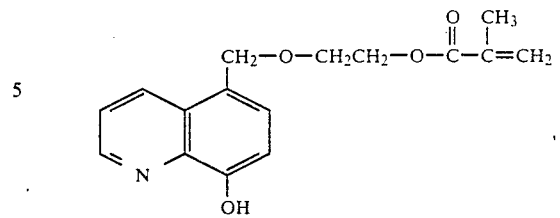

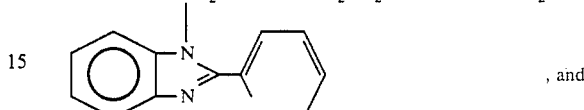

, and

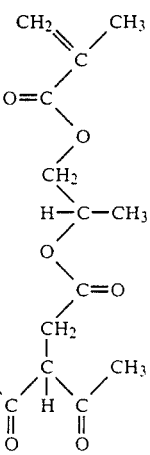

5. A compound having the formula:

$$CH_2=C-C-O-X-W$$
with $R^1$ and $O$ above the central carbons wherein $R^1$ is H, lower alkyl, chlorinated lower alkyl, CN, or Cl;

X is an organic connecting linkage selected from a single bond and a branched or straight chain aliphatic group of up to 22 carbon atoms, providing that groups of two or more carbon atoms may be interrupted by one phenylene,

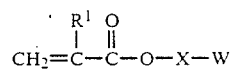

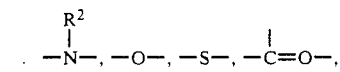

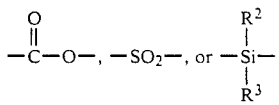

moiety, wherein $R^2$ and $R^3$ are independently H or lower alkyl having 1 to 4 carbon atoms, provided that the total number of atoms of connecting linkage X is not more than 75, and providing that X does not react with W, nor enter into any chelating action, nor have polymerizing units within it; and W is a bidentate chelating moiety selected from the group consisting of

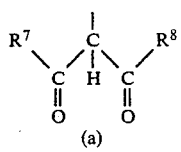

(a)

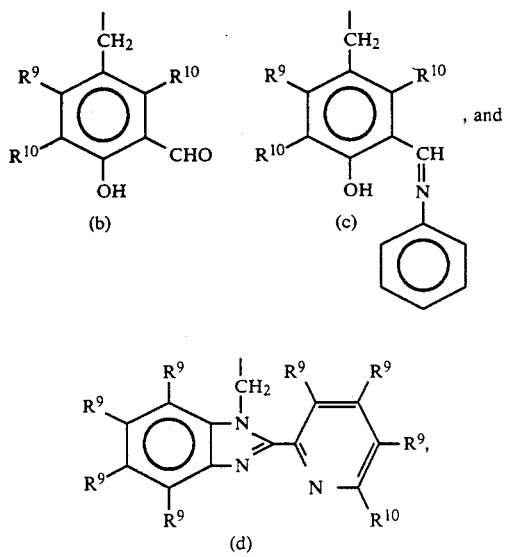

(b)　　　　(c)

(d)

wherein $R^7$, $R^8$ are independently lower alkyl ($c_1$-$C_4$);
$R^9$ is independently selected from a hydrogen atom, a halogen atom selected from fluorine, chlorine, bromine and iodine, an $NO_2$ group, an alkyl group having 1 to 10 carbon atoms, an alkoxy group having 1 to 10 carbon atoms, an alkylthio group having 1 10 carbon atoms, a phenyl group, and a phenyl group substituted with up to 3 groups chosen from a halogen atom, an $NO_2$ group, and a lower alkyl group having 1 to 4 carbon atoms;
$R^{10}$ is independently selected from a hydrogen atom, a halogen atom selected from fluorine, chlorine and bromine, an $NO_2$ group, an alkyl group having 1 to 10 carbon atoms, an alkoxy group having 1 to 4 carbon atoms, and an alkylthio group having 1 to 4 carbon atoms, and a phenyl group.

6. A compound having the formula

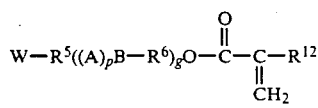

wherein

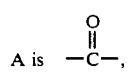

B is a single bond, —O—, —S—, —$NR^2$—, —$SiR^2$-$R^3$—, or phenylene, wherein $R^2$ is H or lower alkyl, and wherein $R^3$ is H or lower alkyl independently of $R^2$;
$R^6$ is an alkylene group having 1 to 10 carbon atoms, or an alkylene group having 1 to 10 carbon atoms which is substituted with up to 3 alkyl groups having 1 to 4 carbon atoms;
$R^5$ is a single bond or $R^6$;

$R^{12}$ is hydrogen or a methyl group;
p is an integer having a value of 0 or 1;
g is an integer having a value of 0 or 1; and
w is a bidentate chelating moiety selected from the group consisting of

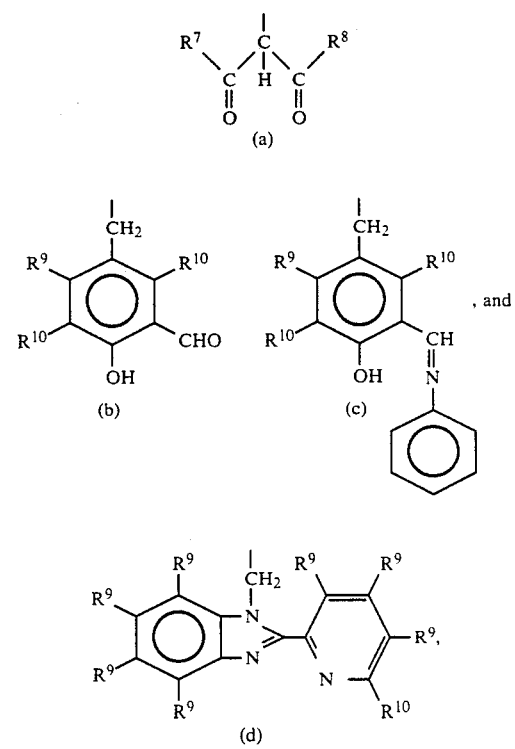

(a)

(b)　　　　(c)

(d)

wherein
$R^7$ and $R^8$ are independently a lower alkyl group having 1 to 4 carbon atoms; and
$R^9$ is independently selected from a hydrogen atom, a halogen atom selected from fluorine, chlorine, bromine, and iodine, an $NO_2$ group, an alkyl group having 1 to 10 carbon atoms, an alkoxy group having 1 to 10 carbon atoms, a phenyl group, and a phenyl group substituted with groups chosen from a halogen atom, an $NO_2$ group, and a lower alkyl group having 1 to 4 carbon atoms; and
$R^{10}$ is independently selected from a hydrogen atom, a halogen atom selected from fluorine, chlorine and bromine, an $NO_2$ group, an alkyl group having 1 to 10 carbon atoms, an alkoxy group having 1 to 4 carbon atoms, an alkylthio group having 1 to 4 carbon atoms, and a phenyl group.

7. The compound according to claim 5 having the formula

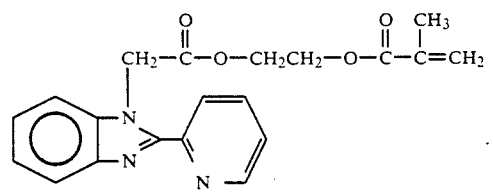

8. A compound having a formula selected from

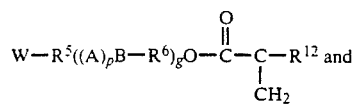

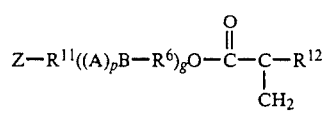

wherein

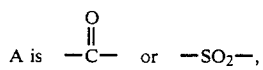

B is a single bond, —O—, —S—, —NR²—, or phenylene, wherein R² is H or lower alkyl;
R⁶ is an alkylene group having 1 to 10 carbon atoms, or an alkylene group having 1 to 10 carbon atoms which is substituted with up to 3 alkyl groups having 1 to 4 carbon atoms;
R⁵ is a single bond or R⁶;
R¹² is hydrogen or a methyl group;
p is an integer having a value of 0 or 1;
g is an integer having a value of 0 or 1; and
w is a bidentate chelating moiety selected from the group consisting of

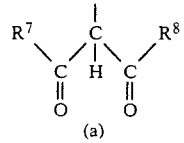

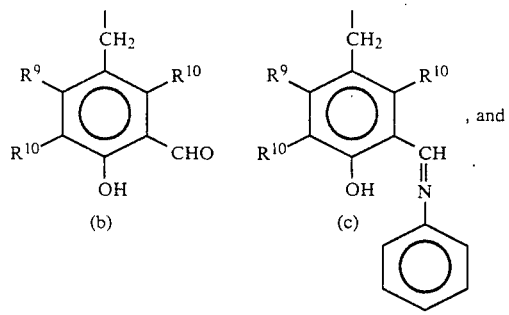

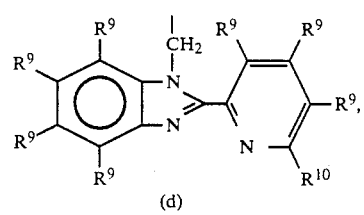

wherein
R⁷ and R⁸ are independently a lower alkyl group having 1 to 4 carbon atoms; and
R⁹ is independently selected from a hydrogen atom, a halogen atom selected from fluorine, chlorine, bromine, and iodine, an NO₂ group, an alkyl group having 1 to 10 carbon atoms, an alkoxy group having 1 to 10 carbon atoms, a phenyl group, and a phenyl substituted with groups chosen from a halogen atom, an NO₂ group, and a lower alkyl group having 1 to 4 carbon atoms; and
R¹⁰ is independently selected from a hydrogen atom, a halogen atom selected from fluorine, chlorine and bromine, an NO₂ group, an alkyl group having 1 to 4 carbon atoms, an alkylthio group having 1 to 4 carbon atoms, and a phenyl group;
R¹¹ is a single bond or —(CH₂)₁₋ₘR⁶—, wherein g and R⁶ are as defined above; and Z is a bidentate chelating moiety selected from the group

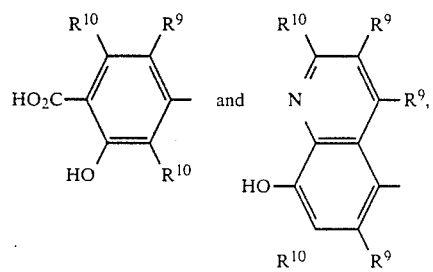

wherein R⁹ and R¹⁰ are as defined above; with the proviso that when B is —S—, then A can only be

9. A compound having the formula

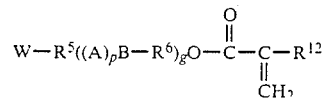

wherein

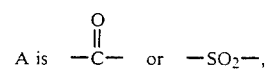

B is a single bond, —O—, —S—, —NR², or phenylene, wherein R² is H or lower alkyl;
R⁶ is an alkylene group having 1 to 10 carbon atoms, or an alkylene group having 1 to 10 carbon atoms which is substituted with up to 3 alkyl groups having 1 to 4 carbon atoms;
R⁵ is a single bond or R⁶;
R¹² is hydrogen or a methyl group;
p is an integer having a value of 0 or 1;
g is an integer having a value of 0 or 1; and
w is a bidentate chelating moiety selected from the group consisting of

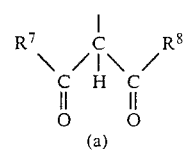

-continued

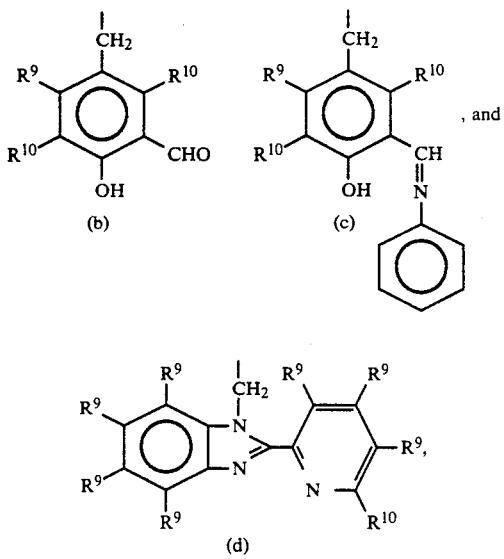

wherein
R⁷ and R⁸ are independently a lower alkyl group having 1 to 4 carbon atoms; and
R⁹ is independently selected from a hydrogen atom, a halogen atom selected from fluorine, chlorine, bromine, and iodine, an NO₂ group, an alkyl group having 1 to 10 carbon atoms, an alkoxy group having 1 to 10 carbon atoms, a phenyl group, and a phenyl group substituted with groups chosen from a halogen atom, an NO₂ group, and a lower alkyl group having 1 to 4 carbon atoms; and
R¹⁰ is independently selected from a hydrogen atom, a halogen atom selected from fluorine, chlorine and bromine, an NO₂ group, an alkyl group having 1 to 10 carbon atoms, an alkoxy group having 1 to 4 carbon atoms, an alkylthio group having 1 to 4 carbon atoms, and a phenyl group.

10. A compound having the formula

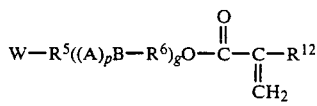

wherein

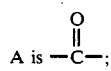

B is a single bond, —O—, —S—, —NR²—, —SiR²-R³—, or phenylene, wherein R² is H or lower alkyl, and wherein R³ is H or lower alkyl independently of R²;
R⁶ is an alkylene group having 1 to 10 carbon atoms, or an alkylene group having 1 to 10 carbon atoms which is substituted with up to 3 alkyl groups having b 1 to 4 carbon atoms;
R⁵ is a single bond or R⁶;
R¹² is hydrogen or a methyl group;
p is an integer having a value of 0 or 1;
g is an integer having a value of 0 or 1; and
w is

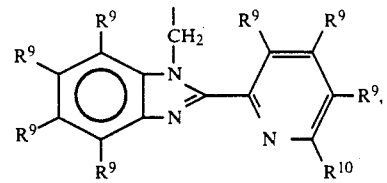

wherein
R⁹ is independently selected for a hydrogen atom, a halogen atom selected from fluorine, chlorine, bromine, and iodine, an NO₂ group, an alkyl group having 1 to 10 carbon atoms, an alkoxy group having 1 to 10 carbon atoms, a phenyl group, and a phenyl group substituted with groups chosen from a halogen atom, an NO₂ group, and a lower alkyl group having 1 to 4 carbon atoms; and
R¹⁰ is independently selected from a hydrogen atom, a halogen atom selected from fluorine, chlorine and bromine, an NO₂ group, an alkyl group having 1 to 10 carbon atoms, an alkoxy group having 1 to 4 carbon atoms, an alkylthio group having 1 to 4 carbon atoms, and a phenyl group.

11. A compound having the formula

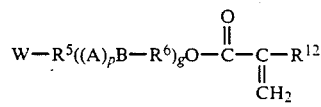

wherein

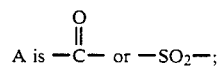

B is a single bond, —O—, —S—, —NR²—, or phenylene, wherein R² is H or lower alkyl;
R⁶ is an alkylene group having 1 to 10 carbon atoms, or an alkylene group having 1 to 10 carbon atoms which is substituted with up to 3 alkyl groups having 1 to 4 carbon atoms;
R⁵ is a single bond or R⁶;
R¹² is hydrogen or a methyl group;
p is an integer having a value of 0 or 1;
g is an integer having a value of 0 or 1; and
w is

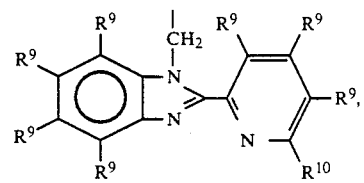

wherein
R⁹ is independently selected from a hydrogen atom, a halogen atom selected from fluorine, chlorine, bromine, and iodine, an NO₂ group, an alkyl group having 1 to 10 carbon atoms, an alkoxy group having 1 to 10 carbon atoms, a phenyl group, and a phenyl group substituted with groups chosen from a halogen atom, an NO₂ group, and a lower alkyl group having 1 to 4 carbon atoms; and $R^{10}$ is independently selected from a hydrogen atom, a halogen atom selected from fluorine, chlorine and bromine, an $NO_2$ group, an alkyl group having 1 to 4 carbon atoms, an alkoxy group having 1 to 4 carbon atoms, and a phenyl group.
12. A compound selected from the group consisting of
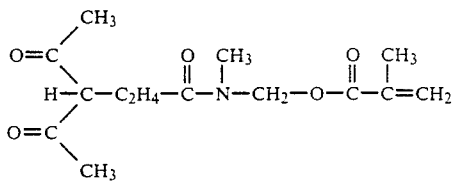
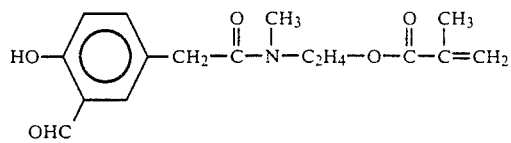
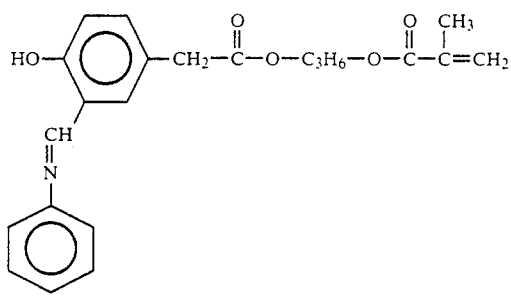
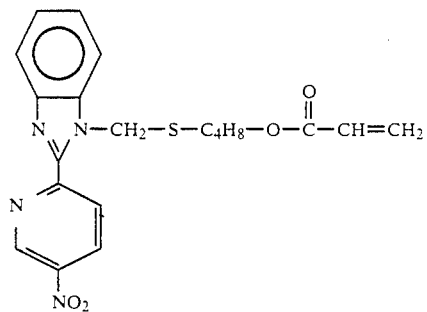
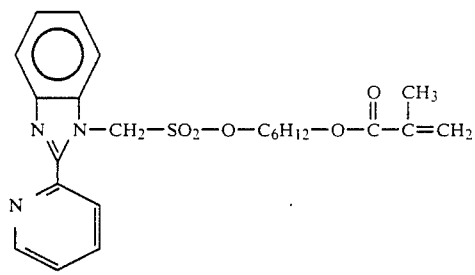
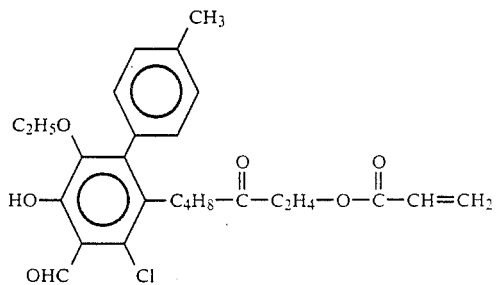

-continued
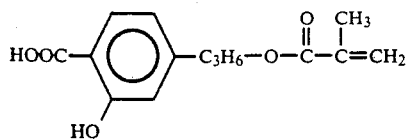
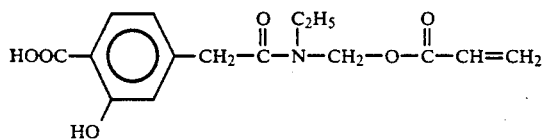
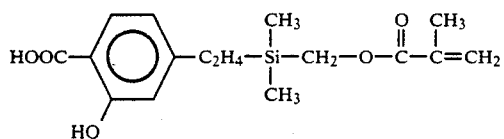
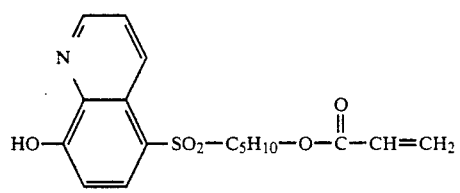
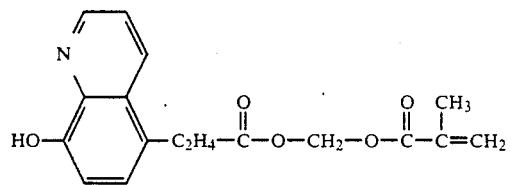
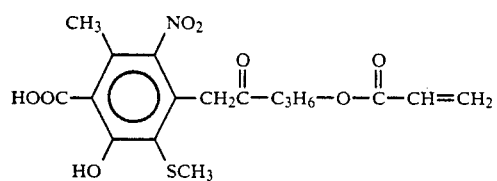
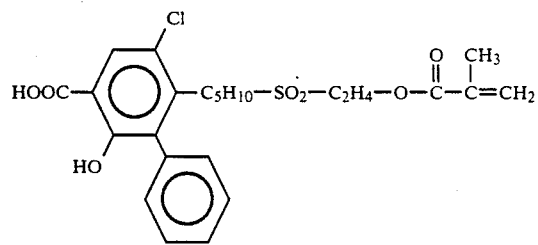
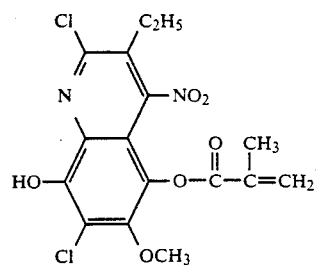

-continued
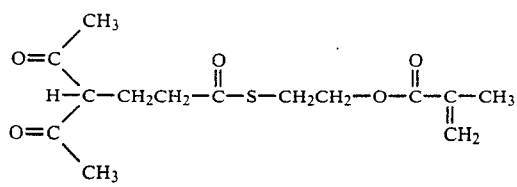
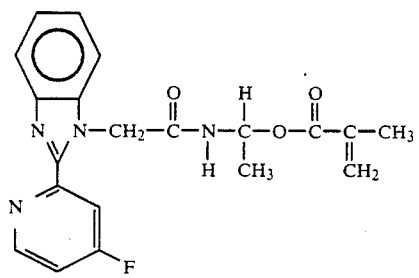
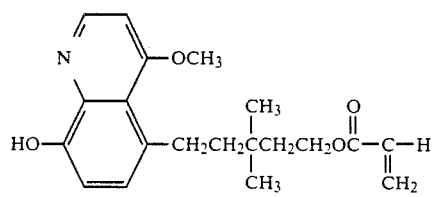
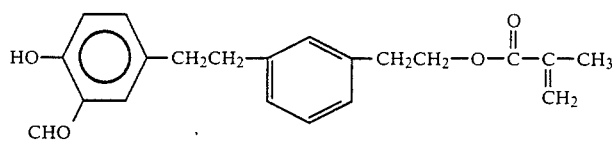
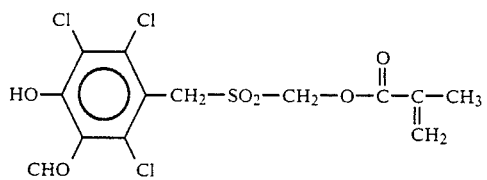
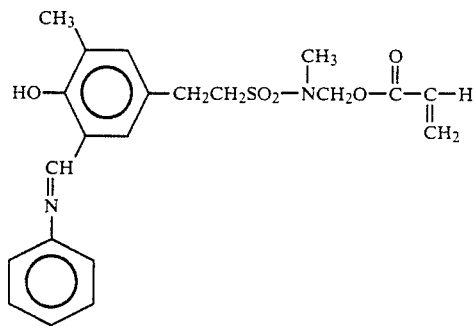
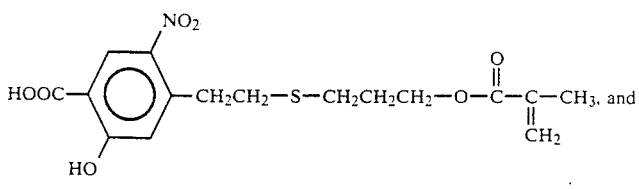

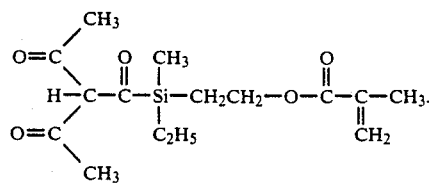
13. A compound having the formula
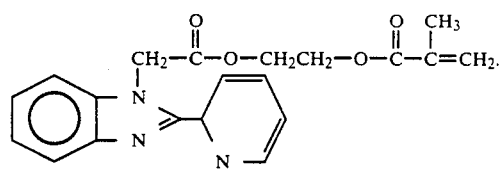
* * * * *

UNITED STATES PATENT AND TRADEMARK OFFICE
CERTIFICATE OF CORRECTION

PATENT NO. : 5,026,860

DATED : June 25, 1991

INVENTOR(S) : Gavin M. Buchan et al.

It is certified that error appears in the above-identified patent and that said Letters Patent is hereby corrected as shown below:

Col. 2, line 64, "Cer." should read -- Ger. --.

Col. 3, line 52, "($C_1$ to $C_4$)," should read -- ($C_1$ to $C_4$), --.

Col. 3, line 55, "an" should read -- any --.

Col. 4, line 52, "($C_1$-$C_4$)," should read --($C_1$ to $C_4$), --.

Col. 24, lines 7-9, "$-\overset{|}{C}=O-$" should read -- $-\overset{|}{C}=O$ --.

Col. 25, line 56, after "$-NR^2-$", insert $-SiR^2R^3-$ --.

Col. 26, line 58, "$NO_2$group" should read -- $NO_2$ group --.

Col. 28, line 54, "$-\overset{|}{C}=O-$" should read -- $-\overset{|}{C}=O$ --.

Col. 29, line 31, "($c_1$-$C_4$)" should read -- ($C_1$-$C_4$) --.

Col. 29, line 37, "1 10 carbon atoms" should read -- 1 to 10 carbon atoms --.

Col. 32, line 57, "w" should be -- W --.

UNITED STATES PATENT AND TRADEMARK OFFICE
CERTIFICATE OF CORRECTION

PATENT NO. : 5,026,860
DATED : June 25, 1991
INVENTOR(S) : Gavin M. Buchan et al.

It is certified that error appears in the above-identified patent and that said Letters Patent is hereby corrected as shown below:

Col. 33, line 63, delete "b" before "1 to 4 carbon atoms".

Col. 33, line 68, "w" should be -- W --.

Col. 36, line 2, after "carbon atoms" insert -- an alkylthio group having 1 to 4 carbon atoms --.

Signed and Sealed this

Nineteenth Day of October, 1993

Attest:

BRUCE LEHMAN

Attesting Officer

Commissioner of Patents and Trademarks